United States Patent [19]

McCoy et al.

[11] Patent Number: 5,122,301

[45] Date of Patent: Jun. 16, 1992

[54] ANTIMICROBIAL COMPOSITIONS CONTAINING PROPYLENE CARBONATE AND/OR ETHYLENE CARBONATE AS THE CARRIER SOLVENT

[75] Inventors: William F. McCoy, W. Lafayette; James M. Summerfield, Lafayette, both of Ind.

[73] Assignee: Great Lakes Chemical Corp., W. Lafayette, Ind.

[21] Appl. No.: 756,619

[22] Filed: Sep. 9, 1991

[51] Int. Cl.$^5$ ............................................. C07D 317/00
[52] U.S. Cl. .................................. 252/384; 514/461; 514/463
[58] Field of Search ................ 514/461, 463; 252/384, 252/380

[56] References Cited

FOREIGN PATENT DOCUMENTS 0338439 10/1989 European Pat. Off. .
0338440 10/1989 European Pat. Off. .
0349786 1/1990 European Pat. Off. .
0351195 1/1990 European Pat. Off. .
57-150896 8/1982 Japan .
2292202 12/1990 Japan .

Primary Examiner—Deborah L. Kyle
Assistant Examiner—Valerie Fee
Attorney, Agent, or Firm—Woodard, Emhardt, Naughton Moriarty & McNett

[57] ABSTRACT

Antimicrobial compositions of bromonitrostyrene or system comprising propylene carbonate, ethylene carbonate bromonitroethenylfuran are formed in a carrier solvent or mixtures thereof. The propylene carbonate system may additionally include tetrahydrofurfuryl alcohol. The compositions have good activity and stability, are non-toxic, non-flammable, non-corrosive, odorless, and colorless, and have desirable boiling and flash points and vapor pressure.

20 Claims, 3 Drawing Sheets

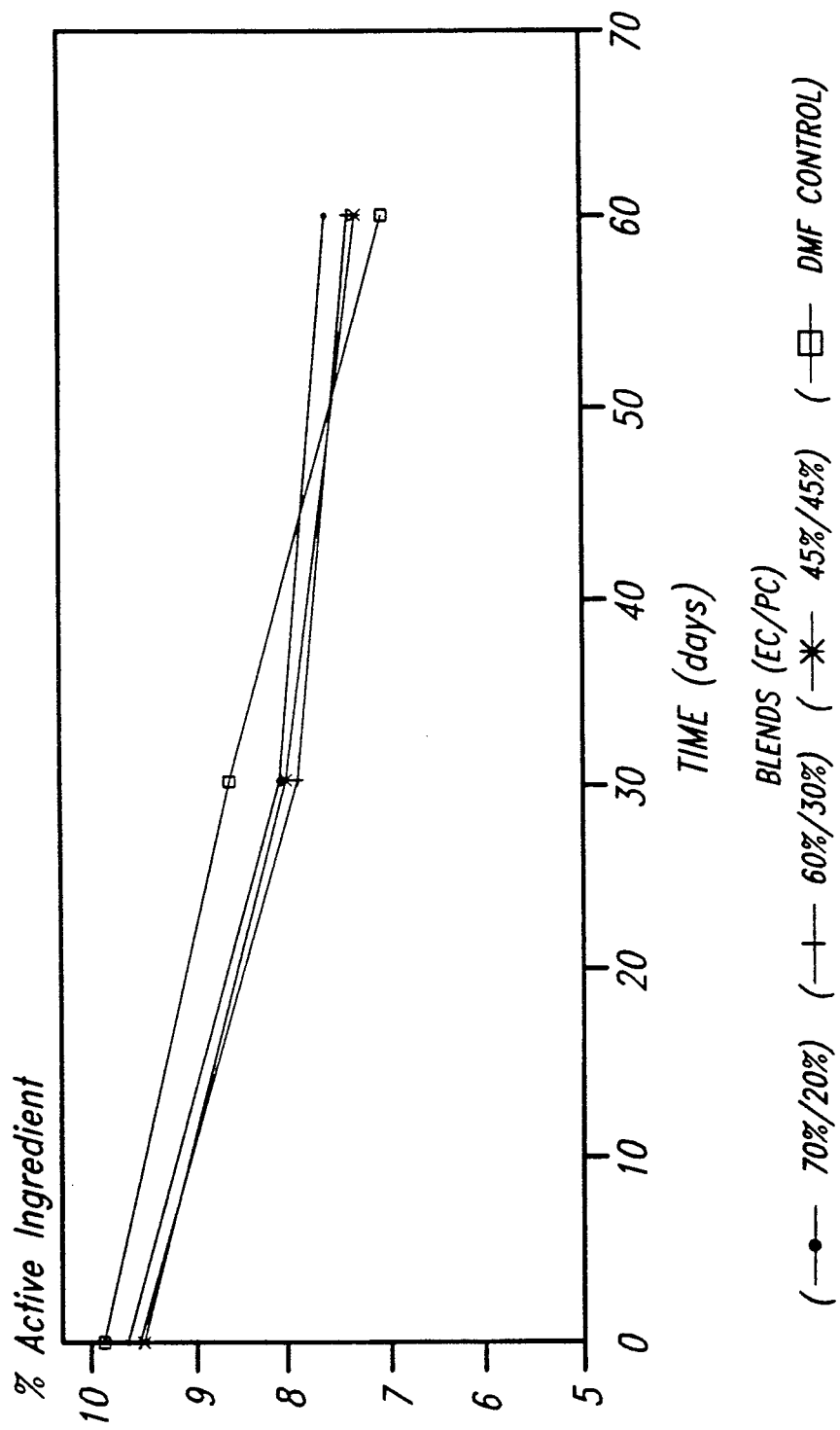

ANTIMICROBIAL COMPOSITIONS CONTAINING PROPYLENE CARBONATE AND/OR ETHYLENE CARBONATE AS THE CARRIER SOLVENT

BACKGROUND OF THE INVENTION

1. Field of the Invention

The present invention relates to the field of antimicrobial compositions of bromointrostyrene and bromonitroethenylfuran, and particularly to carrier solvents for use therewith. 2. Description of the Prior Art Industrial antimicrobials are used to control microbiological fouling of, for example, pulp and paper process waters, certain evaporative cooling waters, air-washers, metal working fluids, cosmetics and toiletries, latex paints, and adhesives. It is common for plant operators and personnel to come in contact with antimicrobials. A stable, non-hazardous formulation is therefore essential. The formulation should be non-toxic, non-flammable, non-corrosive, odorless, colorless, and stable, with a high flash point and good solubility.

One commercial antimicrobial is beta-bromo-beta-nitro styrene (BNS). A current BNS product is a blend of Amsco Solv F and N,N-dimethylformamide (DMF), which is believed to be the only non-oxidizing biocide on the market with a flammable warning label. Amsco Solv F Naptha is 70% heavy aromatic hydrocarbons (e.g. trimethylbenzene and napthalene) and 30% medium aliphatic hydrocarbons. One important user of BNS has unsuccessfully tried for over 5 years to develop a better formulation. Amsco Solv F and DMF both have low boiling points, 178°-214° C. (352°-418° F.) and 153° C. (307° F.), and low flash points, 61° C. (141° F.) and 58° C. (136° F.), respectively. Although Amsco Solv F does not have a measurable vapor pressure, DMF has a vapor pressure of 2.6 mm Hg. The Amsco Solv F and DMF blend also has an undesirable odor.

Dimethylformamide (DMF) has several undesirable properties, and its use in pulp and paper manufacturing has all but ceased in the United States. The oral LD50 for rats is 2.8 g/kg and the dermal LD50 for rabbits is 4720 mg/kg. The 6-hour inhalation ALC is 5000 ppm in rats. The acute effects of exposure to DMF may be caused by inhalation, ingestion, or skin absorption. The vapor or mist from DMF is irritating to the eyes, mucous membranes and upper respiratory tract. The effects of exposure can cause skin irritation, stomach pains, vomiting, diarrhea, nausea, dizziness and headache. Dimethylformamide (DMF) also may cause testicular cancer. When given to female test animals by oral route, by application to skin, by inhalation, or by injection, DMF does not cause fetal malformation, but can produce increased embryo mortality when doses approach the lethal level for the pregnant animal. The OSHA 8-hour Time Weighted Average (TWA) and ACGIH TLV®-TWA for DMF are 10 ppm and 30 mg/m$^3$, respectively. The Du Pont AEL 8 and 12 hour TWA is 10 ppm. All these limits carry a "skin" notation indicating that DMF and vapor can penetrate the mucous membranes. Therefore, control of inhalation alone may not be sufficient to prevent an excessive dose.

Various combinations of antimicrobial agents and carrier solvents have been proposed in the prior art. In some instances, propylene carbonate has been used as a solvent for specific antimicrobials such as chloroisothiazolones, nitrobromopropanes, dichlorodithiolones, dibromonitrilopropionamides and more. See, e.g., European Patent Application Nos. 349786 A1, published Jan. 10, 1990; 351195 A2, published Jan. 17, 1990; 338440 A1, published Oct. 25, 1989; and 338439 A1, published Oct. 25, 1989. The prior art has also described the use of ethylene carbonate as a solvent for certain antimicrobials including maleic anhydride, methylisothiazolones and trichlorohydroxydiphenyl ether. See, e.g., Japanese Patent No. 2292202 A2; European Patent Application No. 349786 A1, published Jan. 10, 1990; and Japanese Patent Application No. 82-150896, filed Aug. 31, 1982. However, the prior art has failed to appreciate the advantageous aspects of the compositions of the present invention.

Despite the efforts in the prior art, there has remained a need for a composition of bromonitrostyrene or bromonitroethenylfuran in a suitable carrier system having desirable physical properties. Such compositions should have low toxicity and be non-flammable, and be stable with a high boiling point and flash point and low vapor pressure. The present invention has overcome the disadvantages of the prior art compositions in providing compositions displaying the foregoing desirable characteristics.

SUMMARY OF THE INVENTION

Briefly describing one aspect of the present invention, there is provided an antimicrobial composition which includes bromonitrostyrene or bromonitroethenylfuran and a carrier solvent comprising propylene carbonate and/or ethylene carbonate. In a related aspect of the invention, the solvent may comprise mixtures of propylene carbonate and tetrahydrofurfuryl alcohol.

It is an object of the present invention to provide antimicrobial compositions of bromonitrostyrene or bromonitroethenylfuran which have good activity and which are stable over time.

Another object of the present invention is to provide antimicrobial compositions which are non-toxic, non-flammable, non-corrosive, odorless and colorless, and which have a high boiling point and flash point and a low vapor pressure.

Further objects and advantages of the present invention will be apparent from the description of the preferred embodiment which follows.

BRIEF DESCRIPTION OF THE DRAWINGS

FIG. 3 is a graph showing the stability of BNS in a carrier system comprising various ratios of ethylene carbonate and propylene carbonate.

DESCRIPTION OF THE PREFERRED EMBODIMENT

For the purposes of promoting an understanding of the principles of the invention, reference will now be made to the preferred embodiments thereof and specific language will be used to describe the same. It will nevertheless be understood that no limitation of the scope of the invention is thereby intended. Alterations and further applications of the principles of the invention are contemplated as would normally occur to one skilled in the art to which the invention relates.

There has remained a desire for an antimicrobial composition of bromonitrostyrene (BNS) or bromonitroethenylfuran (BNEF) in a suitable carrier solvent that results in a stable preparation with extended shelf life. The compositions of the present invention satisfy these preferred attributes, and also are non-toxic, non-flammable, non-corrosive, odorless and colorless, and have a high boiling point and flash point and a low vapor pressure.

The present invention provides compositions of BNS or BNEF with carrier solvents comprising propylene carbonate, ethylene carbonate or mixtures thereof. The compositions may also include combinations of propylene carbonate and tetrahydrofurfuryl alcohol (THFA). BNS and BNEF have been shown to be useful antimicrobials, and the mixtures of the present invention maintain activity of these antimicrobials.

Propylene carbonate (4-methyl-1,3-dioxolan-2-one, or 1,3-carbonyldioxypropane) and ethylene carbonate (1,3-dioxolan-2-one, or 1,3-carbonyldioxyethane) are cyclic organic esters. The Chemical Abstract Service Registry Numbers for propylene carbonate and ethylene carbonate are 108-32-7, and 96-49-1, respectively. The chemical structures are shown below.

Propylene Carbonate

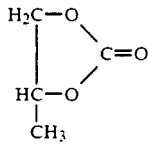

Mol. Wt. 102.09

Ethylene Carbonate

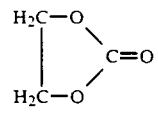

Mol. Wt. 88.06

It has been discovered that propylene carbonate (PC) and ethylene carbonate (EC) are useful as effective carriers for both BNS and BNEF. These carrier solvents combine the features of minimized activity loss for the supported antimicrobials, as well as other desirable aspects forming the objects of the invention. These features include the compositions being characterized by being non-toxic, non-flammable, non-corrosive, odorless and colorless. In addition, the compositions have a high boiling point and flash point and low vapor pressure. Due to the preferred properties of the carrier solvents, the compositions have the foregoing desirable characteristics, and provide good stability and solubility for the antimicrobials.

Figure 1:
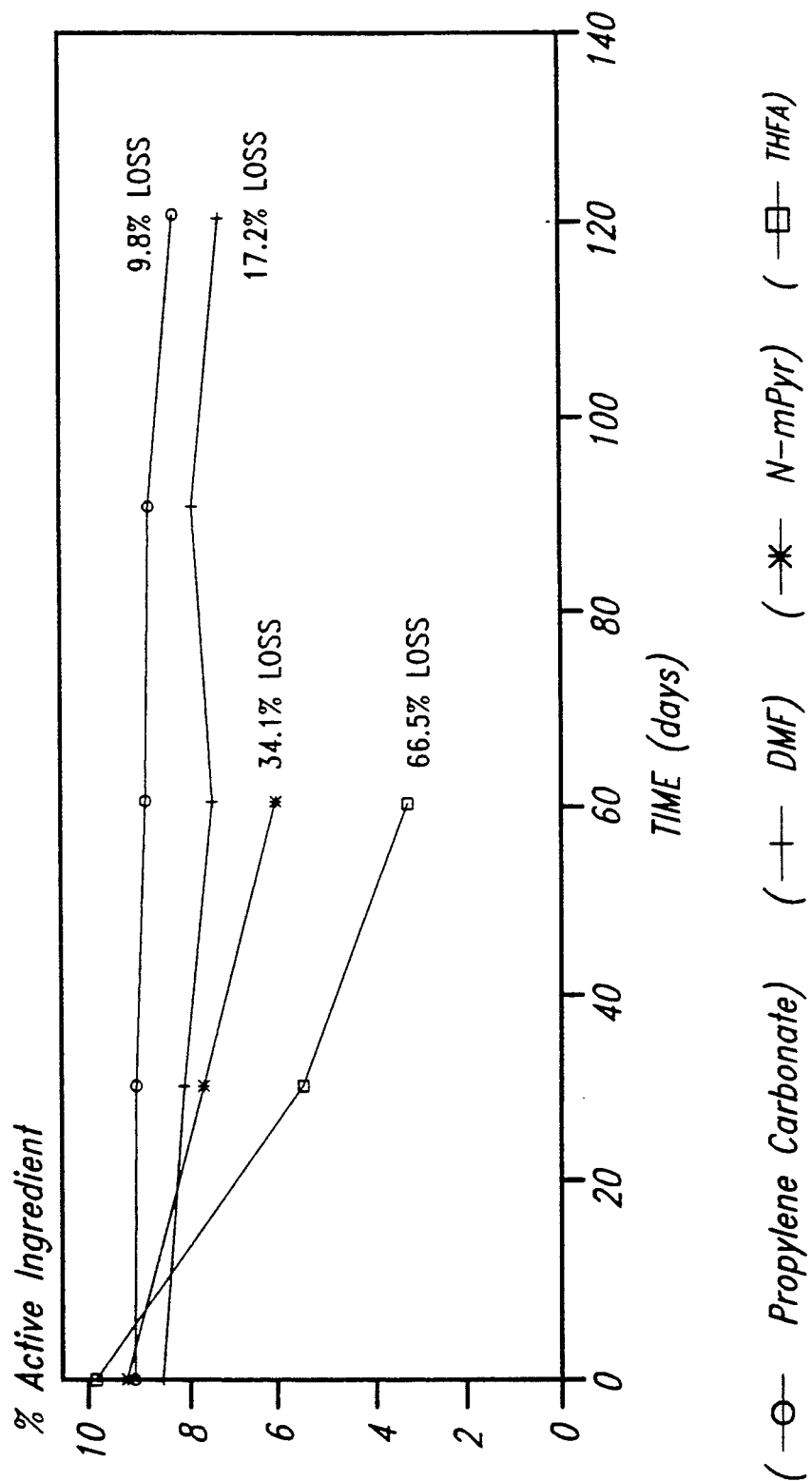
FIG. 1 is a graph showing the stability of BNS in propylene carbonate, particularly in comparison to alternate compositions of the prior art.
Figure 2:
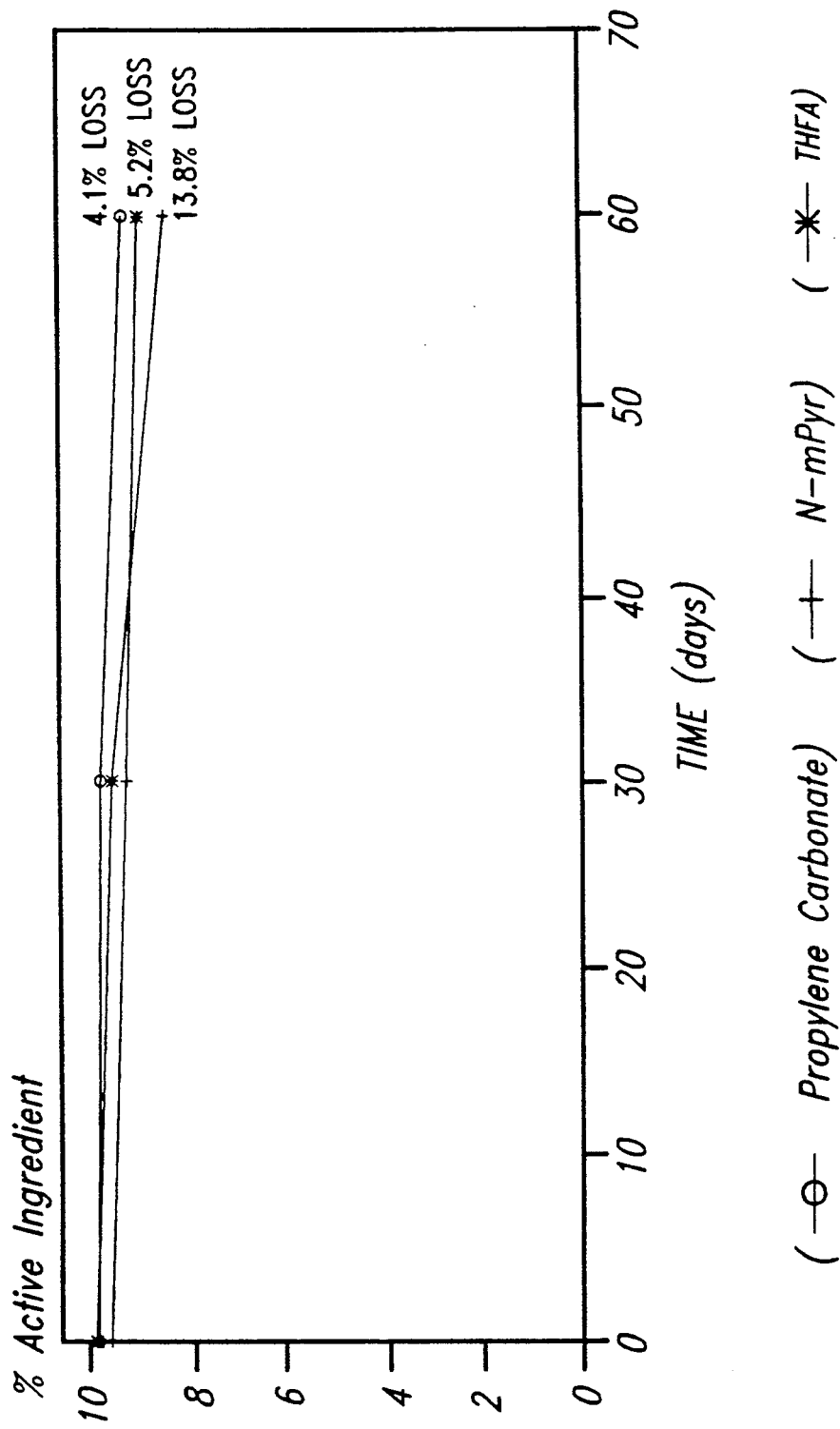
FIG. 2 is a graph comparable to that of FIG. 1, but showing the stability of BNEF in propylene carbonate.

Chemical stability tests were performed to determine if BNS and BNEF were stable in propylene carbonate. The compositions were stored in closed, glass bottles, in a 50° C. incubator. Stable compositions of both BNS and BNEF in propylene carbonate were demonstrated. At 50° C., there was a decline in BNS active ingredient concentration, but the loss was less than 10% active ingredient over 120 days. As shown in FIG. 1, this formulation is almost twice as stable as the analogous N,N-dimethylformamide (DMF) formulation of the type used in the prior art. At 50° C., there was a loss in BNEF active ingredient concentration, but again the loss was minimal, less than 5% over 90 days. As shown in FIG. 2, this formulation showed better than 3 times the stability of the current tetrahydrofurfuryl alcohol (THFA) composition. By comparison, N-methyl pyrrolidinone was tested in formulation with BNS, and surprisingly was found to be incompatible.

Compositions of BNS and BNEF in blends of ethylene carbonate/propylene carbonate (EC/PC) and propylene carbonate/tetrahydrofurfuryl alcohol (PC/THFA) also form desirable formulations. Test compositions were stored in closed, glass bottles in a 50° C. incubator. Stable compositions of BNS were those that showed less active ingredient degradation than the test control (DMF). At 50° C., 10% BNS solutions with EC/PC blends (70%/20%, 60%/30%, and 45%/45%) were tested over 60 days and were shown to be stable. See FIG. 3. None of the BNS solutions tested were stable in the presence of THFA.

The 30 day, 50° C. stability data for 10% BNEF compositions of EC/PC and PC/THFA showed little degradation (Tables 1 and 2). The loss of active ingredient was more prominent in the EC/PC blends, than in the PC/THFA blends. The 90% EC and 80% EC compositions in PC are stable, but are solid at room temperature and are therefore less desirable product compositions. The stability of the other blends is slightly better than the THFA control. See Table 1. The PC/THFA compositions, with the majority being PC, are equally or more stable than the test control (THFA). See Table 2.

TABLE 1

| | Stability of 10% BNEF EC/PC at 50° C. | | | |
|---|---|---|---|---|
| % EC/% PC | Ratio EC:PC | Day 0 | Day 30 | % Loss |
| 90/0* | — | 9.33% | 9.0% | 3.5% |
| 80/10* | 8:1 | 10.01% | 9.2% | 8.1% |
| 70/20 | 3.5:1 | 9.74% | 8.8% | 9.7% |
| 60/30 | 2:1 | 9.97% | 8.8% | 11.7% |
| 45/45 | 1:1 | 8.93% | 8.2% | 8.1% |
| THFA control | — | 9.88% | 8.8% | 11.0% |

*Solid at room temperature

TABLE 2

| | Stability of 10% BNEF PC/THFA at 50° C. | | | |
|---|---|---|---|---|
| % PC/% THFA | Ratio PC:THFA | Day 0 | Day 30 | % Loss |
| 80/10 | 8:1 | 9.82% | 9.6% | 2.2% |
| 70/20 | 3.5:1 | 9.81% | 9.3% | 5.2% |
| 60/30 | 2:1 | 9.94% | 9.4% | 5.4% |
| 45/45 | 1:1 | 10.54% | 8.9% | 15.6% |
| THFA control | — | 9.88% | 8.8% | 11.0% |

Samples of 10% BNS and 10% BNEF (in propylene carbonate) were also evaluated for antimicrobial efficacy. The 10% BNS was aged for 120 days at 50° C. and the 10% BNEF was aged for 60 days. The challenge inoculum was Pseudomonas aeruginosa (ATCC 27853) at a concentration of $1-3 \times 10^6$ colony forming units(cfu)/ml. The Minimum Inhibitory Concentration (MIC) is that concentration which completely inhibited the growth of the challenge inoculum, and the test results are shown in Table 3.

TABLE 3

| SOLUTION | MIC |
|---|---|
| Aged 10% BNS in PC | 13-25 ppm |
| | 13-25 ppm |
| | 25-50 ppm |
| Fresh 10% BNS in PC | 25-50 ppm |
| Aged 10% BNEF in PC | 3-7 ppm |
| | 3-7 ppm |
| | 3-7 ppm |
| Fresh 10% BNEF in PC | 7-13 ppm |
| Propylene Carbonate (PC) | >25,000 ppm |

The aged compounds (Table 3) appear to have a better MIC than the fresh compounds. However, the higher and lower MIC ranges border each other. Hence, the indicated single value MIC for 10% BNS is 25 ppm and for 10% BNEF is 7 ppm. The data shows that BNS and BNEF in propylene carbonate will maintain antimicrobial activity beyond the expected shelf life. At 21° C. (70° F.), the maximum solubility of BNS in neat PC is 29%, and the maximum solubility of BNEF in neat PC is in excess of 55%. Evaluations for BNS or BNEF in percentages from 1% to maximum solubility yield similar results. Also, comparable results are obtained upon evaluation of BNS and BNEF compositions, such as those included in FIGS. 1-3, with ethylene carbonate, blends of ethylene carbonate and propylene carbonate, and blends of PC with THFA.

The compositions of the present invention have desirably low toxicity. For example, the results of acute toxicity testing for propylene carbonate (Texaco Chemical Co.) show that this compound has very low toxicity by single oral and dermal exposure testing. The oral LD50 on rats is >5.0 g/kg and the dermal LD50 on rabbits is >3.0 g/kg. The inhalation LD50 (aerosol) on rats is >5.0 g/m$^3$. The effects of acute eye exposure cause moderate irritation and the effects of acute skin exposure are slight, if any. The acute effects of respiratory exposure are believed to be minimal, also.

Chronic and subchronic studies have determined that propylene carbonate is non-carcinogenic (dermal exposures), does not produce teratogenic effects at maternally (oral) levels, and does not produce any significant toxicity from subchronic (oral) exposures. Previous subchronic (oral) studies using dogs exposed to propylene carbonate have produced anemia, a finding which is similar to that produced by propylene glycol, an FDA Generally Regarded As Safe (GRAS) substance.

Propylene carbonate may contain free propylene oxide (PO) in the range of 5-35 ppm, sometimes higher. Propylene oxide can accumulate in the head space of a container during agitation. However, this phenomenon is not expected to limit the use of PC for antimicrobial applications. The OSHA Permissible Exposure Limit for propylene oxide is 100 ppm for an 8 hour time weighted average exposure.

The present formulations also are characterized by advantageously having a high boiling point and flash point, and a low vapor pressure. This results from the desirable characteristics of the carrier solvents. Propylene carbonate has a high boiling point and a high flash point, 242° C. (468° F.) and 135° C. (275° F.), respectively. Also, propylene carbonate has a low vapor pressure 0.03 mm Hg. Ethylene carbonate has high boiling and flash points of 243° C. (469° F.) and 152° C. (305° F.), respectively. The vapor pressure of ethylene carbonate is 0.01 mm Hg. THFA has boiling and flash points of 178° C. (352° F.) and 74° C. (165° F.), and its vapor pressure is 2.3 mm Hg @ 39° C.

The freezing point of PC is −49.2° C. (−56.6° F.), which is quite low. 10% solutions of BNS and BNEF in PC were cooled to −60° C. (−76° F.) with no crystallization observed. The same compositions were heated to a temperature of 85° C. (185° F.) with no observable gas evolution or discharge. Also, PC is miscible in water at approximately 25%.

The compositions of the present invention are compatible with numerous container materials. As a primary example, propylene carbonate is compatible with many types of materials, although it is incompatible with a few types as well. Compatible container materials include stainless steel, carbon steel, Teflon, EPR, neoprene, natural rubber, cork and polyethylene. Propylene carbonate is believed to be incompatible with Buna-n, Hypalon, Viton and PVC.

In view of the above, it will be seen that the several objects of the invention are achieved and other advantageous results attained. As various changes could be made in the above process, compositions and systems without departing from the scope of the invention, it is intended that all matter contained in the above description shall be interpreted as illustrative and not in a limiting sense.

What is claimed is:

1. An antimicrobial composition comprising:
   an antimicrobial selected from the group consisting of bromonitrostyrene and bromonitroethenylfuran; and
   a carrier solvent selected from the group consisting of propylene carbonate, ethylene carbonate and mixtures thereof.

2. The composition of claim 1 in which the solvent comprises propylene carbonate.

3. The composition of claim 2 and which includes up to about 10% of the antimicrobial.

4. The composition of claim 2 in which the solvent consists essentially of propylene carbonate.

5. The composition of claim 2 and which further includes tetrahydrofurfuryl alcohol.

6. The composition of claim 5 in which the ratio of propylene carbonate to tetrahydrofurfuryl alcohol is from about 1:1 to about 8:1.

7. The composition of claim 5 in which the solvent consists essentially of a mixture of propylene carbonate and tetrahydrofurfuryl alcohol.

8. The composition of claim 1 in which the solvent comprises ethylene carbonate.

9. The composition of claim 8 and which includes up to about 50% of the antimicrobial.

10. The composition of claim 1 in which the solvent comprises a mixture of propylene carbonate and ethylene carbonate.

11. The composition of claim 10 and which includes up to about 10% of the antimicrobial.

12. The composition of claim 10 and which is liquid at room temperature.

13. The composition of claim 12 in which the ratio of ethylene carbonate to propylene carbonate is from about 1:1 to about 3.5:1.

14. The composition of claim 10 in which the solvent consists essentially of a mixutre of ethylene carbonate and propylene carbonate.

15. The composition of claim 14 in which the ratio of ethylene carbonate to propylene carbonate is from about 1:1 to about 3.5:1.

16. In an antimicrobial composition of bromonitrostyrene or bromonitroethenylfuran and a carrier solvent, the improvement comprising the carrier solvent comprising propylene carbonate, ethylene carbonate and mixtures thereof.

17. The improvement of claim 16 in which the carrier solvent comprises propylene carbonate.

18. The improvement of claim 16 in which the carrier solvent comprises propylene carbonate and tetrahydrofurfuryl alcohol.

19. The improvement of claim 16 in which the carrier solvent comprises a mixture of ethylene carbonate and propylene carbonate.

20. The improvement of claim 19 in which the ratio of ethylene carbonate to propylene carbonate is from about 1:1 to about 3.5:1.

* * * * *